United States Patent
Merk et al.

(10) Patent No.: US 10,463,351 B2
(45) Date of Patent: Nov. 5, 2019

(54) TRANSITIONAL GEOMETRY FOR AN EXPANDABLE MEDICAL DEVICE

(71) Applicant: Cook Medical Technologies LLC, Bloomington, IN (US)

(72) Inventors: James C Merk, Terre Haute, IN (US); Brent A Mayle, Spencer, IN (US); Dean R Puckett, Bloomington, IN (US); Darin Voorhies, Bloomington, IN (US); Seoggwan Kim, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 921 days.

(21) Appl. No.: 14/875,232

(22) Filed: Oct. 5, 2015

(65) Prior Publication Data
US 2016/0106405 A1   Apr. 21, 2016

Related U.S. Application Data

(60) Provisional application No. 62/064,273, filed on Oct. 15, 2014.

(51) Int. Cl.
| | |
|---|---|
| *A61B 17/00* | (2006.01) |
| *A61M 1/00* | (2006.01) |
| *A61B 17/221* | (2006.01) |
| *A61F 2/962* | (2013.01) |
| *A61M 25/00* | (2006.01) |
| *A61B 17/29* | (2006.01) |

(52) U.S. Cl.
CPC ..... *A61B 17/00234* (2013.01); *A61M 1/0086* (2014.02); *A61B 17/221* (2013.01); *A61B 2017/00309* (2013.01); *A61B 2017/00464* (2013.01); *A61B 2017/00473* (2013.01); *A61B 2017/00477* (2013.01); *A61B 2017/2215* (2013.01); *A61B 2017/2905* (2013.01); *A61F 2/962* (2013.01); *A61M 25/0074* (2013.01)

(58) Field of Classification Search
CPC ............ A61F 2002/016; A61B 17/221; A61B 2017/2215
See application file for complete search history.

(56) References Cited

U.S. PATENT DOCUMENTS

| | | | | |
|---|---|---|---|---|
| 4,611,594 A | * | 9/1986 | Grayhack et al. ... | A61B 17/221 606/127 |
| 4,737,153 A | * | 4/1988 | Shimamura ........... | A61M 16/04 138/109 |
| 4,969,890 A | * | 11/1990 | Sugita ...................... | A61F 2/88 606/192 |
| 5,438,975 A | * | 8/1995 | Miyagi .............. | A61B 1/00071 600/109 |
| 5,522,819 A | * | 6/1996 | Graves ................. | A61B 17/221 606/110 |

(Continued)

*Primary Examiner* — Alexander J Orkin
(74) *Attorney, Agent, or Firm* — Brinks Gilson & Lione

(57) ABSTRACT

A medical instrument is provided including a device having an expandable portion and a transitional portion. The transitional portion has a spiral cut on the outer surface, and is aligned with the distal portion of a catheter. The transitional portion may be secured to the catheter by a sleeve which is coupled to both the catheter and the transitional portion. Alternatively, the portion of the transitional portion having the spiral cut may be embedded within the catheter.

17 Claims, 4 Drawing Sheets

(56) References Cited

U.S. PATENT DOCUMENTS

| | | | | |
|---|---|---|---|---|
| 5,743,891 A * | 4/1998 | Tolkoff | A61M 5/3273 604/164.01 |
| 5,814,064 A * | 9/1998 | Daniel | A61B 17/22031 606/159 |
| 6,068,622 A * | 5/2000 | Sater | A61M 25/0009 604/524 |
| 6,350,266 B1 * | 2/2002 | White | A61B 17/22031 606/110 |
| 6,702,782 B2 * | 3/2004 | Miller | A61M 25/005 138/111 |
| 6,936,041 B2 * | 8/2005 | Viitala | A61M 1/3653 604/508 |
| 2001/0041899 A1 * | 11/2001 | Foster | A61B 17/221 606/127 |
| 2002/0072764 A1 * | 6/2002 | Sepetka | A61B 17/22031 606/200 |
| 2002/0133170 A1 * | 9/2002 | Tsuruta | A61B 17/221 606/127 |
| 2003/0093106 A1 | 5/2003 | Brady et al. | |
| 2005/0020974 A1 | 1/2005 | Noriega et al. | |
| 2006/0052797 A1 * | 3/2006 | Kanamaru | A61B 17/22 606/113 |
| 2006/0058837 A1 * | 3/2006 | Bose | A61B 17/22 606/200 |
| 2006/0064123 A1 | 3/2006 | Bonnette et al. | |
| 2007/0219466 A1 * | 9/2007 | Tremulis | A61M 25/0068 600/585 |
| 2008/0188831 A1 | 8/2008 | Bonnette et al. | |
| 2008/0269774 A1 * | 10/2008 | Garcia | A61B 17/221 606/127 |
| 2010/0016875 A1 * | 1/2010 | Nakao | A61B 17/221 606/159 |
| 2011/0054519 A1 * | 3/2011 | Neuss | A61B 17/0057 606/213 |
| 2011/0106742 A1 | 5/2011 | Pino | |
| 2011/0160763 A1 * | 6/2011 | Ferrera | A61B 17/221 606/200 |
| 2012/0059356 A1 * | 3/2012 | di Palma | A61B 17/221 604/509 |
| 2012/0101510 A1 | 4/2012 | Lenker et al. | |
| 2012/0143239 A1 * | 6/2012 | Aklog | A61B 17/3207 606/200 |
| 2012/0283633 A1 | 11/2012 | Von Hoffmann | |
| 2012/0310214 A1 * | 12/2012 | Hennessy | A61M 25/005 604/527 |
| 2012/0316600 A1 | 12/2012 | Ferrera et al. | |
| 2013/0030461 A1 * | 1/2013 | Marks | A61F 2/013 606/200 |
| 2014/0018840 A1 * | 1/2014 | Morgan | A61F 2/01 606/200 |
| 2015/0297863 A1 * | 10/2015 | Hannon | A61M 25/0009 604/544 |

* cited by examiner

TRANSITIONAL GEOMETRY FOR AN EXPANDABLE MEDICAL DEVICE

CROSS REFERENCE

This application is a continuation of U.S. Provisional Patent Application No. 62/064,273 filed Oct. 15, 2014, the specifications of which are incorporated herein in their entirety by reference.

BACKGROUND

The field of the present invention relates to component couplings for medical devices. Many medical instruments utilize an expandable device positioned on the distal end of the instrument, connected to a catheter, sheath, or wire guide. Often sheaths and catheters are made of a flexible material such as Nylon or PTFE. If the expandable device is made from a more rigid material, such as nitinol or stainless steel, it can be difficult to couple the expandable device to the distal end of a sheath or catheter. Plastics such as nylon or PTFE do not readily couple with metal alloys such as stainless steel or nitinol. Furthermore, the difference in the modulus of elasticity between the metal alloys and plastics employed in the instrument may cause cracking or breaking of the instrument when the device is placed under strain. This is a frequent issue as medical instruments attached to catheters and sheaths frequently are put under a variety of mechanical strains as they are maneuvered through circuitous and narrow intraluminal passages within the body of a patient.

SUMMARY

Further areas of applicability will become apparent from the description provided herein. It should be understood that the description and specific examples are intended for purposes of illustration only and are not intended to limit the scope of the present disclosure.

In one form of the present disclosure, a medical instrument is provided, comprising a device, a catheter, and a sleeve. The device comprises a transitional portion and a second portion. The transitional portion has a spiral cut arranged through the outer surface of the transitional portion. The catheter comprises at least one lumen and a distal portion which is aligned with the transitional portion. The distal portion of the catheter is positioned at least partially within the transitional portion of the device. The sleeve is coupled to the catheter and coupled to the transitional portion, securing the transitional portion of the device to the distal portion of the catheter.

In another form of the present disclosure, a medical instrument is provided comprising a device and a catheter. The device comprises a transitional portion and an expandable portion, and the transitional portion has a spiral cut arranged through the outer surface of the transitional portion. The catheter comprises a wall and at least one lumen. The distal portion of the catheter is aligned with the transitional portion of the device. At least the portion of the transitional portion comprising the spiral cut is embedded within the wall of the catheter.

In yet another form of the present disclosure, a medical instrument is provided comprising a device, a catheter, and a sleeve. The device comprises a transitional portion and an expandable portion, and the transitional portion has a spiral cut arranged through an outer surface of the transitional portion. The catheter comprises a distal portion which is aligned with the transitional portion, wherein the distal portion is positioned at least partially within the transitional portion. The sleeve has an inner surface which is coupled to the outer surface of the distal portion of the catheter. The transitional portion is embedded within the sleeve so that at least a portion of the sleeve passes through the spiral cut of the transitional portion.

BRIEF DESCRIPTION OF SEVERAL VIEWS OF THE DRAWINGS

The invention may be more fully understood by reading the following description in conjunction with the drawings, in which.

The drawings described herein are for illustration purposes only and are not intended to limit the scope of the present disclosure in any way.

DETAILED DESCRIPTION

Figure 1:
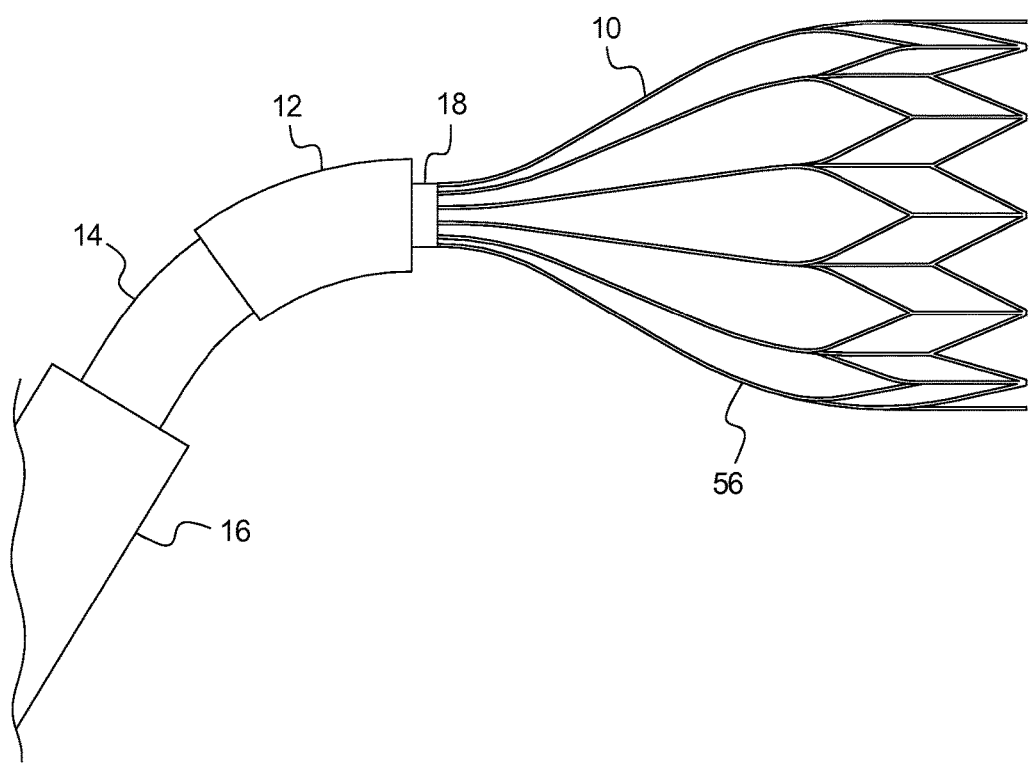
FIG. 1 is a side plan view of a medical instrument, showing an expandable device, a catheter, a sleeve, and a sheath.

Referring now to the drawings, and particularly to FIG. 1, a medical instrument is shown comprising an expandable device 10, a catheter 14, a sheath 16, and a sleeve 12 which secures the expandable device 10 to the catheter 14. The sheath 16 may be used to control the expansion of the expandable device 10.

The expandable device 10 may be cut from a single cannula which may be made of a rigid material. The expandable device 10 comprises an expandable portion 56 and a transitional portion 18. The expandable portion 56 shown in FIG. 1 is an aspiration funnel which is expandable to a diameter larger than the cannula which it is cut from, however, the expandable device 10 is not limited to aspiration funnels but may comprise any expandable device 10 designed to be used within an intraluminal passage, such as a clot retrieval basket, self-expanding stent, temporary shunt. Further, the device may comprise a non-expandable device such as a biopsy needle, a device usable in an atherectomy procedure, or any other device which comprises a rigid distal portion and a flexible proximal portion. The rigid distal portion may be more rigid than the flexible proximal portion.

The expandable portion 56 of the expandable device 10 may also be cut from the cannula so that it may be compressed to have a smaller diameter. The expandable device 10 may be made of nitinol, stainless steel, or some other material which is more rigid than the material comprising the catheter 14.

It may be desirable that the expandable portion 56 of the expandable device 10 is heat set in the expanded position so that when the expandable device 10 is used with a sheath 16, the sheath 16 may be used to control the expansion of the expandable portion 56. The sheath 16 may be initially positioned over the expandable portion 56 to minimize the diameter of the expandable portion 56. The sheath 16 may then be retracted proximally, to expose the expandable portion 56 and allow expansion.

The catheter 14 comprises an outer wall which defines at least one lumen 32, although more than one lumen may be used for a wire guide or for the inflation of a balloon. A distal portion of the catheter 14 may be aligned with the transitional portion 18 so as to at least partially overlap. The catheter 14 may be made of PTFE, nylon, urethanes, vinyls, polyimides, or another material which is more flexible than the material comprising the transitional portion 18 of the expandable device 10

The sleeve 12 is positioned over at least a portion of where the distal portion of the catheter 14 and the transitional portion 18 of the expandable device 10 overlap. It may be desirable that the sleeve 12 extends proximally or distally beyond this overlapping area to increase the bond between the sleeve 12 and the transitional portion 18 or between the sleeve 12 and the catheter 14. The sleeve 12 may be made of the same or similar material as the catheter 14 to increase the ease of bonding the sleeve 12 to the catheter 14 and to ensure that the catheter 14 and the sleeve 12 have similar flexibility under strain. The sleeve 12 may be tubular in shape or may comprise a plurality of strips arranged circumferentially about the overlapping area between the transitional portion 18 of the expandable device 10 and the distal portion of the catheter 14.

Alternatively, the distal end of the catheter 14 may be coupled to the proximal end of the sleeve 12. In such an embodiment, the catheter 14 would not overlap with the transitional portion 18 of the expandable device 10. This configuration may be desirable to allow a catheter diameter which is greater than or equal to the sleeve diameter.

It may be desirable that the sleeve 12 also comprise a covering portion which extends distally from the transitional portion 18 to cover a portion of the expandable portion 56 of the expandable device. This covering may be coupled to the expandable portion 56 is such a way as to expand when the expandable device 10 is deployed. The covering portion may be advantageous to further secure the expandable device 10 to the catheter 14. Additionally, the covering portion may act as a net or blockage, controlling the flow of blood or particulate matter within an intraluminal passage when the expandable device 10 is deployed. In an embodiment wherein the expandable device 10 comprises an aspiration catheter, it may be desirable that the covering is configured to completely seal off the intraluminal passage when the expandable device 10 expands. This would create an advantageous environment within the intraluminal passage distal to the covering, increasing the suction effectiveness of the aspiration catheter.

Alternatively, the covering portion may comprise a separate portion from the sleeve 12 which is only bonded or partially embedded within the sleeve 12. This configuration may be advantageous so that the covering might have a thinner width than the sleeve 12, while minimizing production costs of the instrument.

Figure 2:
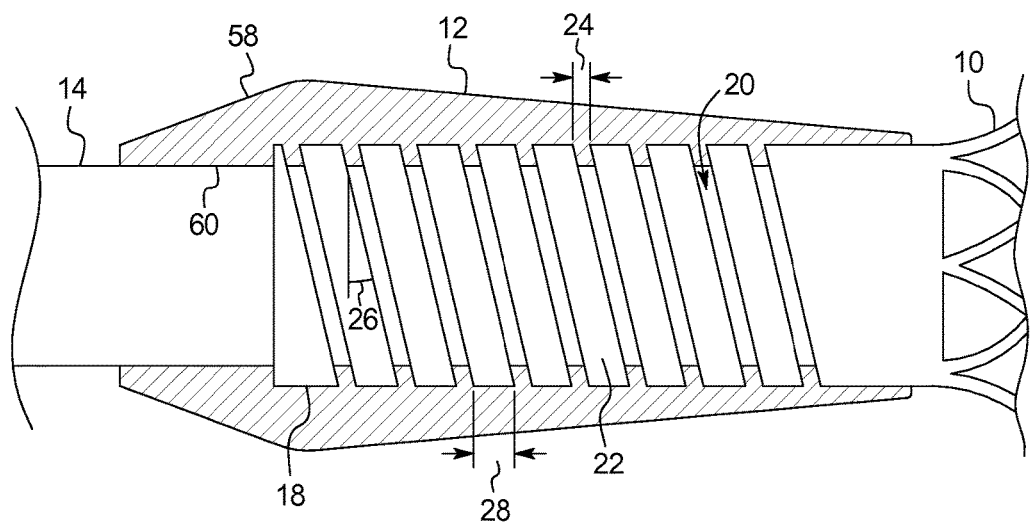
FIG. 2 is a partial cross-sectional view of a transitional portion within a medical instrument, showing an expandable device, a sleeve, and a catheter.

Referring to FIG. 2, a cross-sectional view of the transitional area 18 of the expandable device 10 is shown including a spiral cut 20 arranged longitudinally through the outer surface. The spiral cut 20 creates a spiral portion 22 of the transitional portion 18 which wraps around the circumference of the proximal end of the expandable device 10 and extends distally.

In the embodiment shown in FIG. 2, the transitional portion 18 of the expandable device 10 is cylindrical and has a larger diameter than the distal portion of the catheter 14. Therefore, the distal portion of the catheter 14 overlaps with the transitional portion 18 of the expandable device 10 by being positioned within at least a portion of the transitional portion 18. The sleeve 12 has an outer surface 58 with a diameter greater than the transitional portion 18 of the expandable device 10, and an inner surface 60 with a diameter less than the transitional portion 18. The inner surface 60 of the sleeve 12 is coupled to the outer surface of the catheter 14. As a result, when the sleeve 12 is coupled to the transitional portion 18 and the catheter 14, the inner surface 60 of the sleeve 12 is positioned within the transitional portion 18 and the outer surface 58 of the sleeve 12 is positioned outside of the transitional portion 18. At least a portion of the sleeve 12 passes through the spiral cut 20. It may be desirable that the sleeve 12 is positioned so that the sleeve 12 passes through the entire spiral cut 20, to prevent the expandable device 10 from unscrewing from the sleeve 12.

The coupling of the sleeve 12 to the transitional portion 18 of the expandable device 10 shown in FIG. 2 allows the expandable device 10 to be made from a rigid material and still retain flexibility within the transitional portion 18. The expandable device 10 may be made from a rigid first material such as nitinol or stainless steel. Although the material may not be flexible under strain, the spiral cut 20 in the transitional portion 18 substantially increases the flexibility of the spiral portion 22 of the transitional portion 18, depending on the characteristics of the spiral cut 20.

When the transitional portion 18 is embedded within the sleeve 12 so that a portion of the sleeve 12 passes through or fills the spiral cut 20, the flexibility of the transitional portion 18 is determined by the flexibility of a second material which comprises the sleeve 12. If the sleeve 12 comprises a more flexible material than the material of the expandable device 10, then the transitional portion 18 will have greater flexibility than it would have had without the spiral cut 20, but less flexibility than the sleeve 12 when unsecured to the transitional portion 18.

Several characteristics of the spiral cut 20 also contribute to the flexibility of the transitional portion 18 of the expandable device 10. If the cut width 24 of the spiral cut 20 is wider, the flexibility of the transitional portion 18 will be greater. If the spiral width 28 of the spiral portions 22 is thinner, the flexibility of the transitional portion 18 will be greater. The cut angle 26 of the spiral cut 20 can also be a determining factor. A smaller cut angle 26 will result in very narrow spirals about the circumference of the transitional portion 18, leading to greater flexibility in the spiral portion 22. However, a smaller cut angle 26 requires more spirals to cover the entire transitional portion 18, which might raise the cost of manufacturing the spiral cut 20.

The spiral cut 20 shown in the embodiment in FIG. 2 has a constant cut width 24. Additionally, the spiral portion 22 has a constant spiral width 28 between each spiral of the spiral cut 20. If both the cut width 24 and spiral width 28 are constant, the transitional portion 18 may have a more uniform flexibility from the proximal end of the spiral portion 22 to the distal end of the spiral portion 22. Depending on the characteristics of the expandable device 10, this may be desirable to prevent breaking or cracking of the sleeve 12, catheter 14, or transitional portion 18 while the expandable device 10 is being moved through tortuous passageways.

It may be desirable to vary the thickness of the sleeve 12 from the proximal end to the distal end to further control the flexibility and stability of the transitional portion 18. A thick sleeve 12 is less likely to be cracked, but offers less flexibility. As shown in FIG. 2, the sleeve 12 has a maximum thickness where the expected strain on the transitional portion 18 may be greatest, preventing cracking and breaking of the transitional portion 18. Proximally and distally from this point of maximum thickness, the sleeve 12 tapers to a minimum thickness on the proximal and distal ends, providing more flexibility to those portions of the transitional portion 18. If more support is needed near the proximal end of the sleeve 12, the sleeve 12 may have a thickness which decreases as the sleeve 12 extends distally. However, if more support is needed near the distal end of the sleeve 12, the sleeve 12 may have a thickness which increases as the sleeve 12 extends distally. Moreover, the latter configuration may be beneficial if the sleeve 12 comprises a covering portion extending beyond the transitional portion 18 of the expandable device 10 and onto the expandable portion 56.

Figure 3:
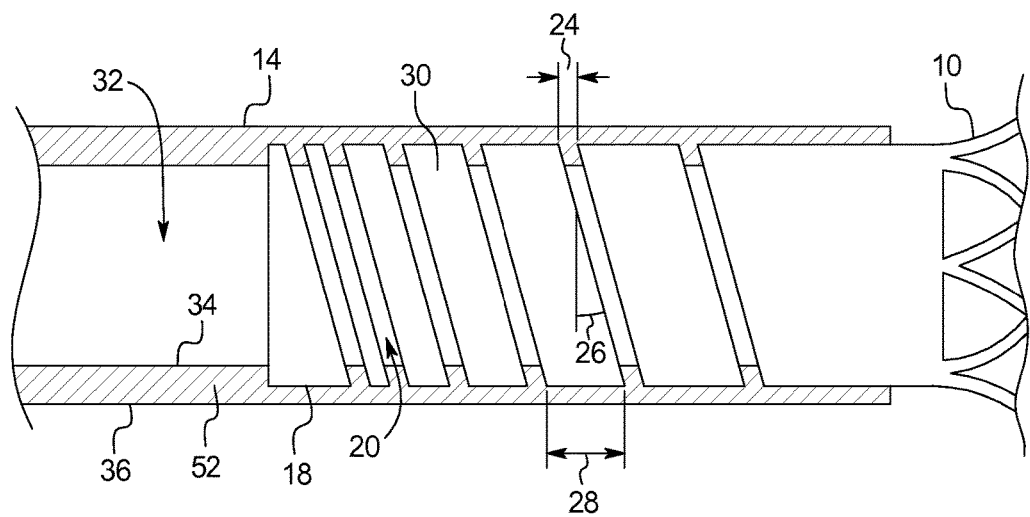
FIG. 3 is a partial cross-sectional view of a transitional portion within a medical instrument, showing an expandable device and a catheter.

Referring to FIG. 3, another embodiment of the transitional portion 18 of the expandable device 10 is shown. In the embodiment shown, the sleeve 12 is excluded and the transitional portion 18 is embedded within the wall 52 of the catheter 14. The wall 52 of the catheter 14 comprises an outer surface 36 and an inner surface 34. The inner surface 34 of the wall 52 defines at least one lumen 32 of the catheter 14, through which a guide wire or other device may be passed. At least the portion of the transitional portion 18 which has the spiral cut 20 is embedded within the wall 52 of the distal portion of the catheter 14 so that the inner surface 34 of the wall 52 is inward from the inner surface of the transitional portion 18, and the outer surface 36 is outward from the outer surface of the transitional portion 18. As a result, at least a portion of the wall 52 passes through at least a portion of the spiral cut 20 of the transitional portion 18, coupling the expandable device 10 to the catheter 14.

The embodiment shown in FIG. 3 also comprises a spiral cut 20 which has a changing cut angle 26, creating a spiral portion 30 in the transitional portion 18 of increasing spiral width 28 extending distally. Despite the cut angle 26 changing, the cut width 24 remains constant, creating consistent flexibility wherever the spiral cut 20 passes through. The configuration of this embodiment may be advantageous as it results more separated areas of flexibility on the distal portions of the transitional portion 18. If the area of highest strain is near the proximal end of the transitional portion 18, such a configuration may be advantageous in providing relief near the proximal end and gradually distributing it distally.

Figure 4:
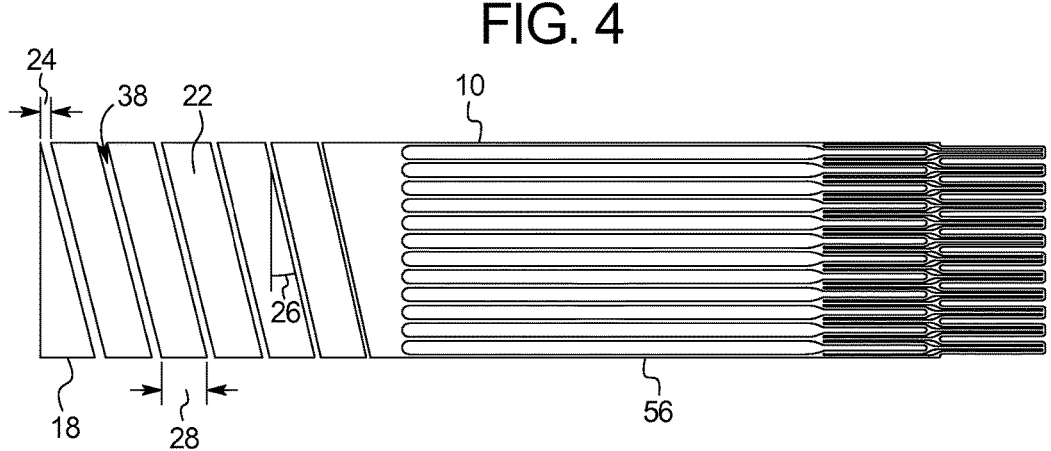
FIG. 4 is a side plan view of an expandable device, showing an expandable portion and a transitional portion.

Referring to FIG. 4, an embodiment of an expandable device 10 is shown in a compressed state. In this embodiment, the transitional portion 18 comprises a spiral cut 38 with a diminishing cut width 24 as the spiral cut 38 extends distally. The cut angle 26 and the spiral width 28 of the spiral portions 22 remain consistent throughout the length of the spiral cut 38.

The embodiment shown may be advantageous in providing increasing rigidity extending distally in the transitional portion 18. Where the cut width 24 of the spiral cut 38 narrows, the flexibility of the spiral portion 22 will decrease. This may be effective in evenly distributing or reducing the strain on the transitional portion 18 of the expandable device 10 and ensure that the transitional portion 18 bends smoothly while under strain.

Figure 5:
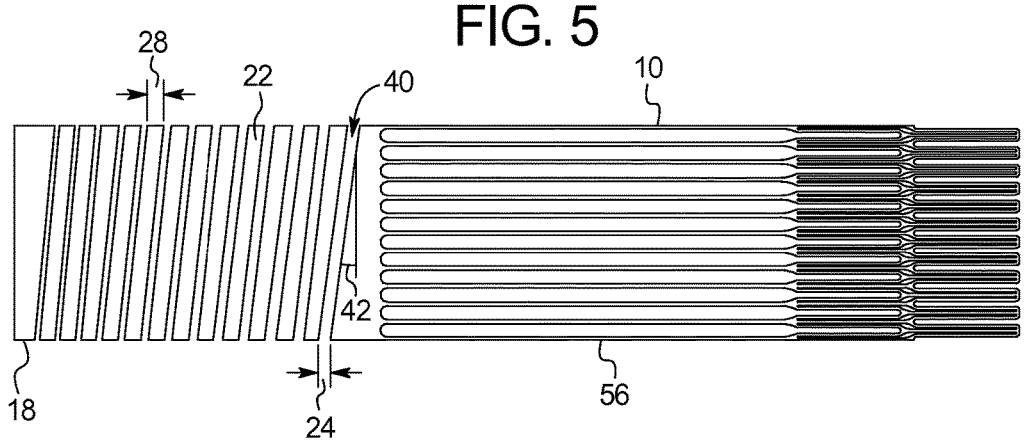
FIG. 5 is a side plan view of an expandable device, showing an expandable portion and a transitional portion.

Referring to FIG. 5, an embodiment of an expandable device 10 is shown in a compressed state. In this embodiment, the transitional portion 18 comprises a spiral cut 40 with an expanding cut width 24 as the spiral cut 40 extends distally. in the embodiment shown, the backwards cut angle 42 of the spiral cut 40 may be reversed from the cut angles 26 shown in FIGS. 2-4, 6, and 7. The backwards cut angle 42 and spiral width 28 of the spiral portion 22 remain consistent through the length of the spiral cut 40.

The embodiment shown may be advantageous in providing increasing flexibility extending distally in the transitional portion 18. This configuration may be effective in distributing or reducing strain on the transitional portion 18 of the expandable device 10. If the expandable portion 56 of the expandable device 10 is more rigid than the transitional portion 18, this configuration may also be useful in allowing the distal end of the transitional portion 18 to be bent at sharper angles to properly direct the expandable portion 56 through narrow passages and around difficult curves within the intraluminal passage.

Figure 6:
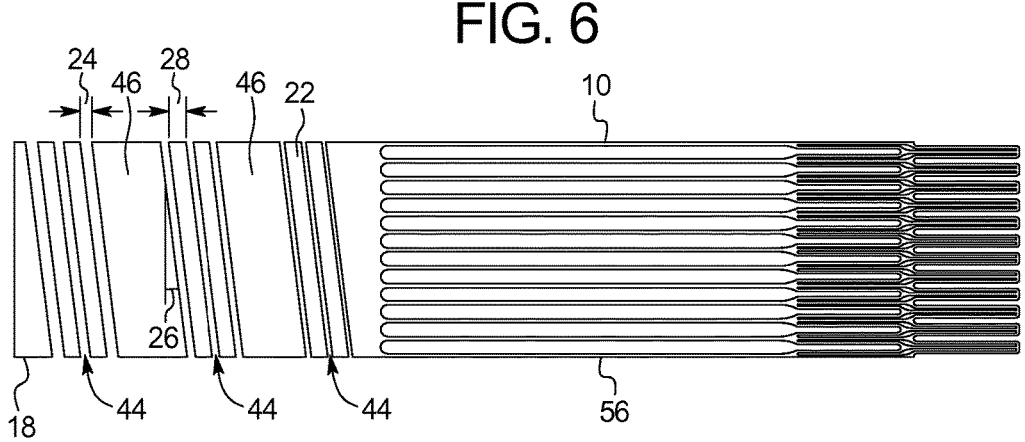
FIG. 6 is a side plan view of an expandable device, showing an expandable portion and a transitional portion.

Referring to FIG. 6, an embodiment of an expandable device 10 is shown in a compressed state. In this embodiment, the transitional portion 18 comprises three segmented spiral cuts 44. Each segmented spiral cut 44 is separated from the other segmented spiral cuts 44 by at least one uncut segment 46. The uncut segments 46 provide rigidity to the structure of the transitional portion 18 and additional longitudinal support to the expandable portion 56 of the expandable device 10, if needed. The cuts may be arranged with a decreasing cut width 24 proceeding distally, which would produce a similar effect to the embodiment shown in FIG. 4. The cuts may also be arranged to have increasing cut width 24 distally to produce a similar effect to the embodiment shown in FIG. 5.

The embodiment shown may be useful in distributing strain away from particular areas of the transitional portion 18 which may be vulnerable to cracking or breaking. Positioning a segmented spiral cut 44 in a high strain area allows increased flexibility for the spiral portion 22 in that area, distributing the strain to the areas of the transitional portion 18 proximal and distal to the segmented spiral cut 44. Positioning of the segmented spiral cuts 44 may also define where the transitional portion 18 bends more or less when being moved through a narrow intraluminal passage.

Figure 7:
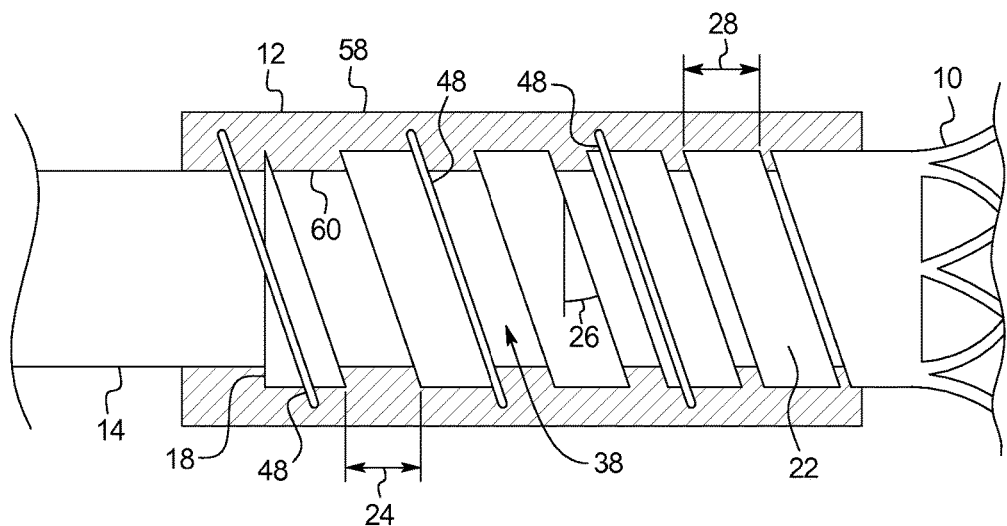
FIG. 7 is a partial cross-sectional view of a transitional portion within a medical instrument, showing an expandable device, a sleeve, a support member, and a catheter.

Referring to FIG. 7, a cross-sectional view of an embodiment of the transitional portion 18 is shown, wherein a filament 48 is embedded within the sleeve 12 as a support member. The filament 48 spirals around the circumference of the sleeve 12, increasing the overall rigidity of the sleeve 12. This increased rigidity may assist the sleeve 12 to securely couple with the transitional portion 18 of the expandable device 10 to prevent cracking or breaking under strain. Depending on the rigidity needed, the sleeve 12 may comprise multiple filaments 48 separated longitudinally to form supported segments. Alternatively, multiple filaments 48 may be angularly separated to form a double or triple helix within the sleeve 12. Additionally, it may not be desirable that the filament 48 spirals around the circumference of the sleeve 12. Instead, it may be desirable to include several filaments 48 spaced in straight lines about the circumference of the sleeve 12. Although the filament 48 shown in FIG. 7 is within a sleeve 12, the filament 48 could also be embedded in a catheter 14 regardless of whether a sleeve 12 is included in the embodiment.

Figure 8:
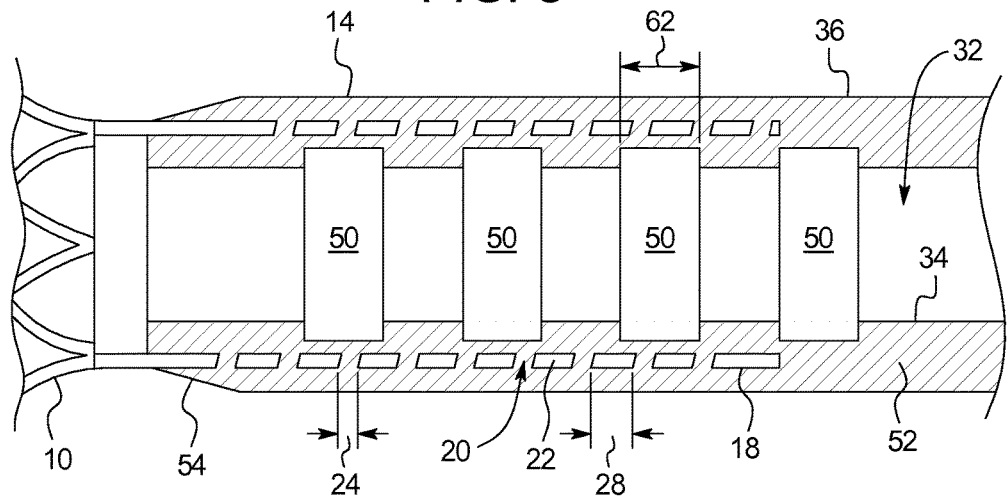
FIG. 8 is a partial cross-sectional view of a transitional portion within a medical instrument, showing an expandable device, support members, and a catheter.

Referring to FIG. 8, a cross-sectional view of an embodiment of the transitional portion 18 is shown, wherein the transitional portion 18 is embedded within the wall 52 of the catheter 14 and a plurality of bands 50 are also embedded within the wall 52 of the catheter 14 as support members. The bands 50 may be positioned under the transitional portion 18, as shown, or over the transitional portion 18.

The bands 50 may be made of a rigid material such as nitinol or stainless steel, and extend around the circumference of the catheter 14. The bands 50 have a band width 62 which defines a length of the catheter 14 with increased rigidity. The bands 50 may be positioned at areas of the transitional portion 18 which may be more vulnerable to cracking or breaking under high strain. When the transitional portion 18 is under strain, the bands 50 distribute the strain proximally and distally into the less rigid areas adjacent to the bands 50. A plurality of bands 50 may be desirable to distribute strain across multiple portions of the transitional portion 18. Although the bands 50 shown in FIG. 8 are embedded in a catheter 14, the bands could also be embedded within a sleeve 12, if one is included in the embodiment.

Accordingly, it is now apparent that there are many advantages of the invention provided herein. In addition to the advantages that have been described, it is also possible that there are still other advantages that are not currently recognized but which may become apparent at a later time.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to embrace them.

We claim:

1. A medical instrument, comprising:
    a device comprising a transitional portion and a second portion, the transitional portion comprising a spiral cut arranged through an outer surface of the transitional portion, wherein the transitional portion and the second portion are formed from a single cannula, and the spiral cut is spaced apart from the second portion;
    a catheter comprising at least one lumen and a distal portion, wherein the entire spiral cut of the transitional portion is aligned along and affixed to a length of the distal portion of the catheter and the second portion extends distally from the distal portion of the catheter, and the second portion is a clot retrieval basket which is expandable to a diameter which is greater than a diameter of the catheter.

2. The medical instrument of claim 1, wherein the spiral cut has a cut width which increases as the spiral cut extends distally.

3. The medical instrument of claim 1, wherein the spiral cut has a cut width which decreases as the spiral cut extends distally.

4. The medical instrument of claim 1, further comprising a sleeve positioned over the transitional portion wherein the sleeve secures the transitional portion of the device to the distal portion of the catheter, and a wall of the sleeve has a thickness which increases as the sleeve extends distally.

5. The medical instrument of claim 1, further comprising a sleeve positioned over the transitional portion wherein the sleeve secures the transitional portion of the device to the distal portion of the catheter, and a wall of the sleeve has a thickness which decreases as the sleeve extends distally.

6. The medical instrument of claim 1, further comprising a sheath including at least one lumen, wherein the catheter and device are positioned within the lumen, and wherein the sheath may be moved proximally to expand the second portion of the device.

7. The medical instrument of claim 1, further comprising a sleeve positioned over the transitional portion wherein the sleeve secures the transitional portion of the device to the distal portion of the catheter, and at least a portion of the sleeve passes through the spiral cut of the transitional portion.

8. The medical instrument of claim 7, wherein the portion of the sleeve which passes through the spiral cut is coupled to an outer surface of the catheter.

9. The medical instrument of claim 1, further comprising a sleeve positioned over the transitional portion wherein the sleeve secures the transitional portion of the device to the distal portion of the catheter, and a support member embedded in the sleeve.

10. The medical instrument of claim 1, further comprising a support member embedded in the catheter.

11. The medical instrument of claim 10, wherein the support member comprises a filament coiled and embedded within the catheter, wherein the filament at least partially overlaps with the transitional portion.

12. The medical instrument of claim 10, wherein the support member comprises a ring embedded within the catheter, wherein the ring at least partially overlaps with the transitional portion.

13. The medical instrument of claim 1, further comprising a sleeve positioned over the transitional portion wherein the sleeve secures the transitional portion of the device to the distal portion of the catheter, and the sleeve comprises a first material and the transitional portion comprises a second material which is less flexible than the first material.

14. The medical instrument of claim 13, wherein the catheter is made of the first material.

15. A medical instrument, comprising:
    a device comprising a transitional portion and an expandable portion, the transitional portion comprising a spiral cut arranged through an outer surface of the transitional portion and spaced apart from the expandable portion; and
    a catheter comprising a wall and at least one lumen, wherein a distal portion of the catheter is aligned with the transitional portion, and wherein the entire spiral cut of the transitional portion is embedded within the wall of the catheter, and the expandable portion is an aspirational funnel which is expandable to a diameter which is greater than a diameter of the transitional portion.

16. The medical instrument of claim 15, wherein the catheter is made of a first material and the transitional portion is made of a second material which is less flexible than the first material.

17. The medical instrument of claim 15, wherein at least a portion of the wall of the catheter passes through the spiral cut of the transitional portion.

* * * * *